(12) United States Patent
Heismann

(10) Patent No.: US 9,492,107 B2
(45) Date of Patent: Nov. 15, 2016

(54) MEDICAL IMAGING APPARATUS WITH A MOVEMENT DETECTION UNIT AND A METHOD FOR DETECTING PATIENT MOVEMENT

(71) Applicant: Björn Heismann, Erlangen (DE)

(72) Inventor: Björn Heismann, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 109 days.

(21) Appl. No.: 14/172,645

(22) Filed: Feb. 4, 2014

(65) Prior Publication Data

US 2014/0221812 A1 Aug. 7, 2014

(30) Foreign Application Priority Data

Feb. 5, 2013 (DE) .................. 10 2013 201 830

(51) Int. Cl.
| *A61B 5/055* | (2006.01) |
| *A61B 5/113* | (2006.01) |
| *A61B 5/11* | (2006.01) |
| *G01R 33/28* | (2006.01) |
| *A61B 5/00* | (2006.01) |

(52) U.S. Cl.
CPC .............. *A61B 5/113* (2013.01); *A61B 5/055* (2013.01); *A61B 5/11* (2013.01); *G01R 33/28* (2013.01); *A61B 5/4205* (2013.01); *A61B 5/7285* (2013.01); *A61B 2562/0219* (2013.01)

(58) Field of Classification Search
CPC ...................................................... A61B 5/113
See application file for complete search history.

(56) References Cited

U.S. PATENT DOCUMENTS

2004/0111025 A1 6/2004 Avniash et al.
2009/0149740 A1 6/2009 Hoheisel

FOREIGN PATENT DOCUMENTS

DE 102007059599 A1 6/2009

OTHER PUBLICATIONS

German Office Action dated Oct. 18, 2013 for corresponding German Patent Application No. DE 10 2013 201 830.4.
Speck, O., Real Time Scanner Control, INUMAC Report OVGU, DE, (Nov. 19, 2012).
Wikipedia, "Beschleunigungssensor"; Wikipedia, freie Enzeklopädie; pp. 1-2 (2013).

*Primary Examiner* — Mark Remaly
(74) *Attorney, Agent, or Firm* — Lempia Summerfield Katz LLC

(57) ABSTRACT

A medical imaging apparatus includes a detector unit, a patient-receiving region enclosed by the detector unit in a cylindrical manner, and a movement detection unit. The movement detection unit has at least one acceleration sensor unit to detect movement of a patient. the at least one acceleration sensor unit has a fastening element to fasten the at least one acceleration sensor unit to a subregion of the patient relevant to a medical imaging examination.

20 Claims, 2 Drawing Sheets

MEDICAL IMAGING APPARATUS WITH A MOVEMENT DETECTION UNIT AND A METHOD FOR DETECTING PATIENT MOVEMENT

This application claims the benefit of DE 102013201830.4, filed on Feb. 5, 2013, which is hereby incorporated by reference in its entirety.

BACKGROUND

The disclosed embodiments relate to a medical imaging apparatus with a detector unit, a patient-receiving region enclosed by the detector unit in a cylindrical manner, and a movement detection unit.

Patient movement in medical imaging (e.g., magnetic resonance imaging), such as swallowing movements, respiratory movements, or involuntary movements of the patient, result in poor image quality in the evaluated image data. The patient movement may also result in longer data acquisition times and, thus, a high level of patient exposure.

Optical cameras are used to monitor the patient or to detect patient movement during a medical imaging examination. However, integration of optical camera systems within a patient-receiving region of medical imaging apparatuses, such as a magnetic resonance apparatus or a computed tomography apparatus, is difficult because of magnetic fields, x-ray radiation, gamma radiation, or a combination thereof.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the disclosed embodiments may provide simple and reliable detection of patient movement during a medical imaging examination.

A medical imaging apparatus includes a detector unit, a patient-receiving region enclosed by the detector unit in a cylindrical manner, and a movement detection unit. The movement detection unit includes at least one acceleration sensor unit to detect patient movement. The acceleration sensor unit has a fastening element to fasten the acceleration sensor unit to a subregion of the patient relevant to a medical imaging examination.

Patient movement may be detected in a subregion to be examined in an efficient and simple manner during the medical imaging examination. Alternatively or additionally, a position of the patient may be monitored efficiently and simply during the medical imaging examination. A swallowing movement and/or a respiratory movement may be detected in a direct and precise manner, inasmuch as the at least one acceleration sensor unit may be disposed directly on the patient (e.g., in a thoracic cage region and/or in a throat region). The at least one acceleration sensor unit may therefore be disposed directly on a moving subregion of the patient to detect the movement. The movement detection unit may have just one acceleration sensor unit for movement detection or may include multiple acceleration sensor units to detect patient movement simultaneously in different positions on the patient. The at least one acceleration sensor unit may be fastened to a patient surface, such as a skin surface. The medical imaging apparatus may be configured as or include a magnetic resonance apparatus, a computed tomography apparatus, a positron emission tomography (PET) apparatus, or other apparatus. The acceleration sensor unit or the acceleration sensor element may be used to detect time-resolved acceleration signals, acceleration data, or both acceleration signals and data of a movement of a subregion of the patient of relevance for the examination, from which movement of the patient (e.g., the sub-region), may be calculated via integration over time of the acceleration signals, acceleration data, or both the acceleration signals and the acceleration data.

The acceleration sensor unit may include at least one microsystem acceleration element. A space-saving acceleration sensor unit may thus be provided for detecting patient movement. A microsystem acceleration element may be configured as or include an acceleration sensor element of microchip size and/or an acceleration sensor element disposed on a microchip. The acceleration sensor element may be configured as, be based on, or include a micro-electromechanical system (MEMS).

An acceleration sensor unit having at least one acceleration element that detects movement (e.g., acceleration) of the patient along at least one spatial direction may achieve direct and simple detection of movement of the patient (e.g., of the subregion of the patient to be examined) along the spatial direction. The acceleration sensor unit may also include an acceleration sensor element that detects a movement (e.g., acceleration) of the patient along at least two different spatial directions. Alternatively or additionally, instead of an acceleration sensor element that detects movement (e.g., acceleration) along at least two different spatial directions, the acceleration sensor unit may include two acceleration sensor elements, each detecting a movement (e.g., acceleration) of the patient along one spatial direction. The spatial directions of the detected movements differ between the two acceleration sensor elements. In one embodiment, the acceleration sensor unit includes at least one energy supply unit, allowing flexible use of the acceleration sensor unit. For example, the energy supply unit may include an energy storage apparatus (e.g., a battery in the form of a button cell). Alternatively, the energy supply unit may also include an energy conversion unit that draws energy for operation of the acceleration sensor unit from an electromagnetic field, gamma radiation, x-ray radiation, or combinations thereof, from the medical imaging apparatus and converts the drawn energy to electrical energy. For example, in a magnetic resonance apparatus, the energy conversion unit may take the energy for operation of the acceleration sensor unit from the electromagnetic field within the patient-receiving region.

A fastening element including an adhesion layer may achieve simple and fast arrangement of the acceleration sensor unit on the patient. The adhesion layer may include a bonding layer, a layer that sticks to the skin of the patient when moistened with a liquid, or both. As a result, the acceleration sensor unit may be removed from the patient by medical personnel in a simple manner after the medical imaging examination.

The movement detection unit may have a data evaluation unit configured to evaluate movement data acquired by the at least one acceleration sensor unit. As a result, patient movement may be determined from the acquired acceleration sensor data directly and, in some cases, independently of a data evaluation unit for evaluating medical image data. The data evaluation unit may be included within (e.g., encompassed by) at least one acceleration sensor unit or may be configured separately from the at least one acceleration sensor unit. The movement detection unit may include a single data evaluation unit configured to evaluate all movement data, acceleration data, or both movement data and acceleration data from all of the acceleration sensor units included within (e.g., encompassed by) the movement detection unit. As a result, the movement detection unit may be compact.

The acceleration sensor unit may include a data transmission unit configured for wireless data transmission, cable-free data transmission, or both wireless and cable-free data transmission with the data evaluation unit. As a result, the movement detection unit may have a flexible arrangement. The arrangement of the movement detection unit may be independent of an arrangement of the data evaluation unit. A space-saving and compact acceleration sensor unit may be provided for detecting movement (e.g., acceleration) of the patient for the medical imaging examination, inasmuch as there is no need for cable guides. The data transmission unit may include at least one send unit, with each of the acceleration sensor units including a send unit of the data transmission unit, and at least one receive unit encompassed by the data evaluation unit. The at least one send unit and the receive unit may be configured for wireless data transmission, cable-free data transmission, or both wireless and cable-free data transmission to the data evaluation unit.

The medical imaging apparatus may also include a system control unit configured to generate a trigger signal for medical image data acquisition as a function of the movement data evaluated by the data evaluation unit. The medical data acquisition may thus be tailored to patient movement (e.g., movement cycles of the patient). For example, patient movement may be presented by respiratory movement, swallowing movement, or both respiratory and swallowing movement. The system control unit may include a data evaluation unit, a data processing unit, or both a data evaluation unit and a data processing unit, directed to generating the trigger signal.

The medical imaging apparatus may include a system control unit configured to generate a correction factor for an evaluation of medical image data as a function of the data evaluated by the data evaluation unit. The correction factor may provide an evaluation of the medical image data with fewer errors. For example, the correction factor may be taken into account in the form of a displacement correction, a rotation correction, or both a displacement correction and a rotation correction during a reconstruction of the medical image data. A correction factor may be useful when movement of the head of the patient occurs during a medical imaging examination of the head region of the patient.

In one embodiment, the acceleration sensor unit may include a further sensor element configured to detect a further patient parameter. The further patient parameter may be, for example, a skin resistance, a heartbeat, a temperature, or any combination thereof of the patient. The further sensor element may allow further patient parameters to be detected in a space-saving and time-saving manner. The further patient parameters may be made available for an extensive and detailed evaluation of the medical image data.

In one or more of the present embodiments, a method for detecting patient movement during a medical imaging examination is provided. The method includes positioning a patient on a patient support apparatus, positioning an acceleration sensor unit on a subregion of the patient to be examined, and introducing the patient support apparatus, together with the patient, into a patient-receiving region of a medical imaging apparatus. The method also includes acquiring medical imaging data using the medical imaging apparatus, and acquiring movement data using the acceleration sensor unit during acquisition of the medical imaging data.

Patient movement in a subregion to be examined may be detected in an efficient and simple manner during the medical imaging examination. Alternatively or additionally, a position of the patient may be monitored efficiently and simply during the medical imaging examination. A swallowing movement, a respiratory movement, or both a swallowing movement and a respiratory movement may be detected in a direct and precise manner, inasmuch as the at least one acceleration sensor unit may be disposed directly on the patient (e.g., in a thoracic cage region, in a throat region, or in both a thoracic cage region and a throat region). The at least one acceleration sensor unit may thus be disposed directly on a moving subregion of the patient to detect the movement.

A correction value may be determined for correction of the medical imaging data based on the acquired movement data. The determination may allow the medical image data to be evaluated with fewer errors.

The generation of the trigger signal based on the acquired movement data may tailor the medical data acquisition to patient movement (e.g., movement cycles of the patient). The patient movement may be formed, for example, by respiratory movement, swallowing movement, or both respiratory and swallowing movement.

BRIEF DESCRIPTION OF THE DRAWINGS

Further advantages, features and details of exemplary embodiments are described below with reference to the drawings.

DETAILED DESCRIPTION OF THE DRAWINGS

Figure 1:
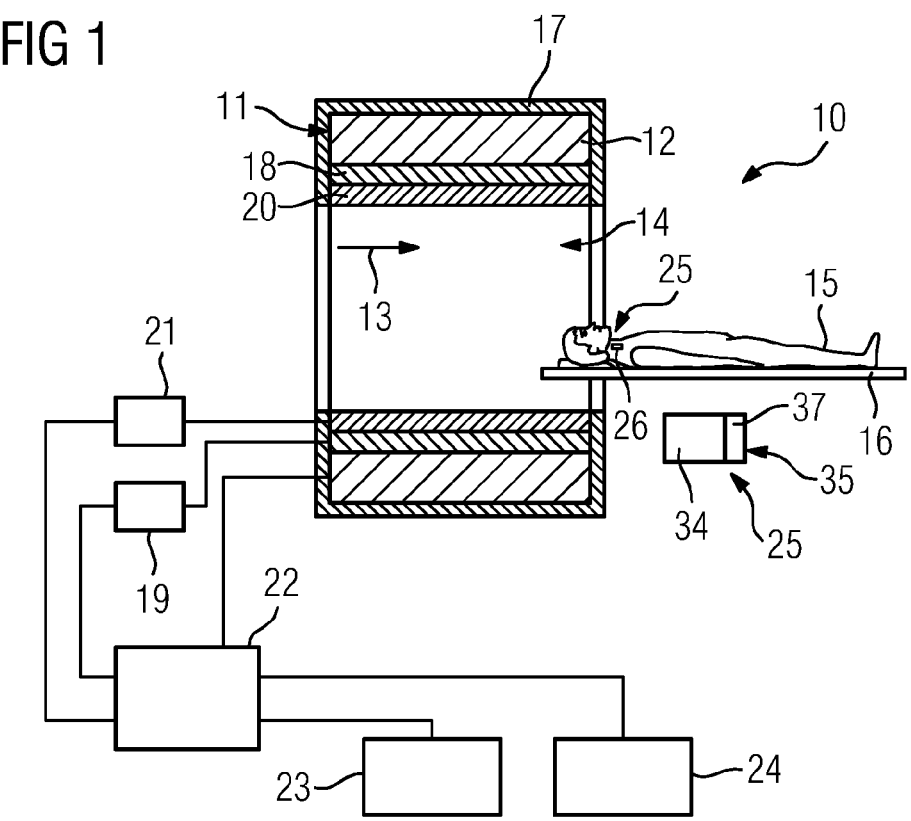
FIG. 1 shows a schematic diagram of one embodiment of a medical imaging apparatus.

FIG. 1 shows a schematic diagram of one embodiment of a medical imaging apparatus 10 configured as a magnetic resonance apparatus. However, the configuration of the medical imaging apparatus 10 is not restricted to a magnetic resonance apparatus. Rather, the medical imaging apparatus 10 may also be configured as, for example, a computed tomography apparatus, a positron emission tomography (PET) apparatus, or an AX arm.

The magnetic resonance apparatus includes a detector unit that, in turn, includes a magnet unit 11 with a main magnet 12 for generating a powerful and, for example, constant main magnetic field 13. The magnetic resonance apparatus also includes a cylindrical patient-receiving region 14 to receive a patient 15. The patient-receiving region 14 is enclosed by the magnet unit in a cylindrical manner in a circumferential direction. The patient 15 may be moved into the patient-receiving region 14 by a patient support apparatus 16 of the magnetic resonance apparatus. The patient support apparatus 16 includes a couch for moving the patient into the patient-receiving region 14. The couch may be disposed movably within the magnetic resonance apparatus. The magnet unit 11 is shielded from the outside by a housing panel 17 of the magnetic resonance apparatus.

The magnet unit 11 also includes a gradient coil unit 18 for generating magnetic field gradients used for spatial encoding during imaging. The gradient coil unit 18 is controlled by a gradient control unit 19. The magnet unit 11 also includes a high-frequency antenna unit 20 and a high-frequency antenna control unit 21 to excite polarization in the main magnetic field 13 generated by the main magnet 12. The high-frequency antenna unit 20 is controlled by the high-frequency antenna control unit 21 and emits high-frequency magnetic resonance sequences into an examination chamber. The examination chamber may correspond with or be formed by the patient-receiving region 14.

To control the main magnet 12 of the gradient control unit 19 and to control the high-frequency antenna control unit 21, the magnetic resonance apparatus includes a system control unit 22 encompassing a computation unit. The system control unit 22 controls the magnetic resonance apparatus centrally, for example, allowing the implementation of a predetermined imaging gradient echo sequence. Control information such as, for example, imaging parameters, as well as reconstructed magnetic resonance images, may be displayed for an operator on a display unit 23 (e.g., at least one monitor) of the magnetic resonance apparatus. The magnetic resonance apparatus may also include an input unit 24, via which information, parameters, or both information and parameters, may be input by an operator during a measurement process.

The medical imaging apparatus 10 may include further components, such as components usually part of medical imaging apparatuses. A detailed description of the mode of operation of a magnetic resonance apparatus known to the person skilled in the art is not provided.

Figure 2:
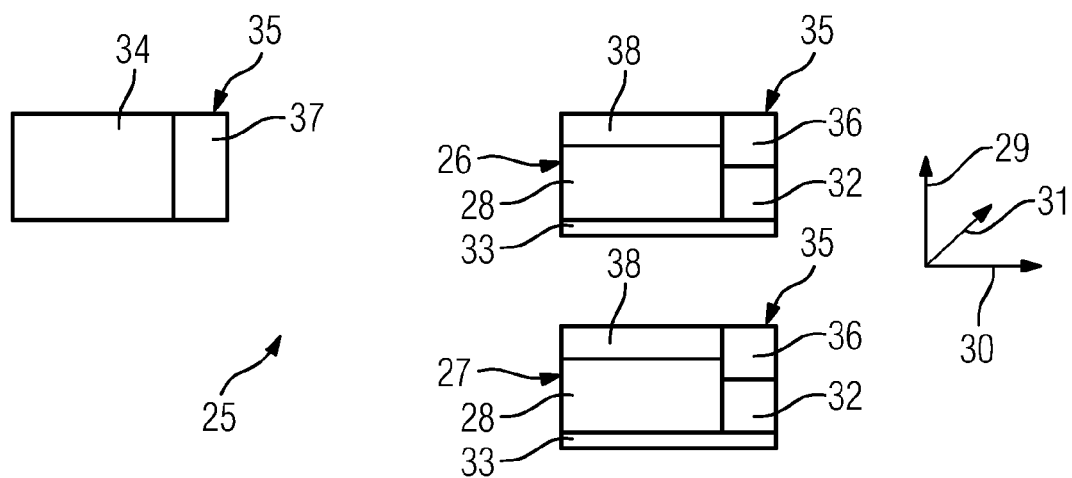
FIG. 2 shows a schematic detailed view of one embodiment of a movement detection unit with a number of acceleration sensor units.
Figure 3:
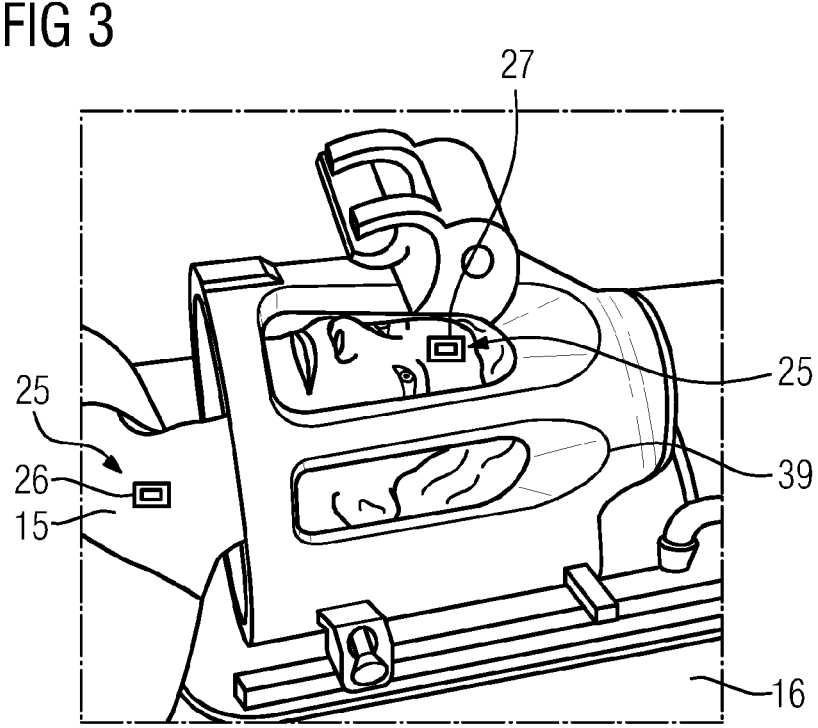
FIG. 3 shows a diagram of an arrangement of acceleration sensor units on a patient in accordance with one embodiment.

To detect movement of the patient 15, the magnetic resonance apparatus includes a movement detection unit 25 (see FIGS. 1-3). In the exemplary embodiments of FIGS. 1-3, the movement detection unit 25 includes a number of acceleration sensor units 26, 27. In some cases, the movement detection unit 25 may also include a single acceleration sensor unit 26 or more than two acceleration sensor units 26, 27. The acceleration sensor units 26, 27 are shown in more detail in FIG. 2. Each acceleration sensor unit 26, 27 includes an acceleration sensor element 28. The acceleration sensor elements 28 are configured to detect a movement (e.g., an acceleration) of the patient 15 (e.g., a subregion of the patient 15 relevant to the magnetic resonance examination) along different spatial directions 29, 30, 31. The different spatial directions 29, 30, 31 may include three spatial directions 29, 30, 31 that are disposed orthogonally to one another. The acceleration sensor elements 28 may be configured as or include a microsystem acceleration sensor element, thereby allowing space-saving positioning of the acceleration sensor units 26, 27 on the patient 15.

Alternatively, at least one of the acceleration sensor elements 28 may also be configured to detect a movement (e.g., an acceleration) of the subregion of the patient 15 relevant to the magnetic resonance examination along a single spatial direction 29, 30, 31.

The acceleration sensor units 26, 27 may also include an energy supply unit 32. Each energy supply unit 32 is configured to supply all of the units and/or modules of a respective one of the acceleration sensor units 26, 27 with electrical energy. Each energy supply unit 32 includes an energy storage apparatus (not shown in detail) in the form of a battery (e.g., a button cell). Alternatively or additionally, each energy supply unit 32 may also include an energy conversion unit to convert energy in the patient-receiving region 14 (e.g., electromagnetic fields, gamma radiation, x-ray radiation, or any combination thereof) to electrical energy to supply the acceleration sensor unit 26, 27 with electricity.

Each acceleration sensor unit 26, 27 includes at least one fastening element 33 to arrange the acceleration sensor units 26, 27 on the patient 15 (e.g., on the subregion of the patient 15 relevant to the magnetic resonance examination). The fastening elements 33 may be used to fasten, dispose, or both fasten and dispose the acceleration sensor units 26, 27 directly on the subregion of the patient 15 relevant to the magnetic resonance examination (see FIGS. 2 and 3). Each fastening element 33 may include an adhesion layer that may include, for example, a bonding layer. The adhesion layers may also be configured such that the adhesion layers are moistened with a liquid before being disposed on the patient 15. The adhesion layers may thus adhere to the skin of the patient 15 via the liquid.

The movement detection unit 25 may also include a data evaluation unit 34 disposed (e.g., configured) separately from the individual acceleration sensor units 26, 27. The data evaluation unit 34 is configured to evaluate the movement data, the acceleration data, or both the movement and acceleration data acquired by the individual acceleration sensor units 26, 27. Data is transmitted between the individual acceleration sensor units 26, 27 and the data evaluation unit 34 by a data transmission unit 35. The data transmission unit 35 includes a number of send units 36. Each send unit 36 is included within or encompassed by one of the acceleration sensor units 26, 27. To receive the acceleration data, movement data, or both acceleration data and movement data transmitted by the send units 36, the data evaluation unit 34 includes a receive unit 37 of the data transmission unit 35. The data transmission unit 35 (e.g., the individual send units 36 and the receive unit 37) may be configured for wireless data transmission, cable-free data transmission, or both wireless and cable-free data transmission between the acceleration sensor units 26, 27 and the data evaluation unit 34.

The data evaluation unit 34 uses the acquired movement data, the acquired acceleration data, or both the acquired movement data and the acquired acceleration data of the patient 15 to determine movement of the patient 15. Double integration of the acceleration data over time takes place within the data evaluation unit 34. The data evaluation unit 34 includes software instructions, computer programs, or both software instructions and computer programs for evaluating the acquired movement data, the acquired acceleration data, or both the acquired movement data and the acquired acceleration data. The data evaluation unit 34 also includes a processor unit (not shown in detail), further units, or both a processor unit and further units to perform the computation operations.

The evaluated movement data is transmitted from the data evaluation unit 34 of the movement detection unit 25 to the system control unit 22 of the magnetic resonance apparatus by a further data transmission unit (not shown in detail). The system control unit 22 includes a data processing unit (not shown in detail) that further processes the movement data evaluated by the data evaluation unit 34 of the movement detection unit 25. For example, the movement data evaluated by the data evaluation unit 34 of the movement detection unit 25 may be used for the generation of a trigger signal from the system control unit 22 for the magnetic resonance examination. Movement data relating, for example, to a swallowing movement, a respiratory movement, or both a swallowing movement and a respiratory movement of the patient 15 may be used for generation of the trigger signal.

The movement data evaluated by the data evaluation unit 34 of the movement detection unit 25 may also be used for movement correction during an evaluation of the medical image data by the system control unit 22. The movement data from the data processing unit of the system control unit 22 may be used to calculate a correction factor for a displacement correction, a rotation correction, or both a displacement correction and a rotation correction. The correction factor may be taken into account by the data processing unit during the reconstruction of the magnetic resonance image data.

In one exemplary embodiment, each acceleration sensor unit 26, 27 includes a further sensor element 38 configured to detect a further patient parameter for the patient 15 during operation of the acceleration sensor units 26, 27. The further sensor elements 38 may be configured to detect a skin resistance of the patient 15, a temperature of the patient 15, a heartbeat of the patient 15, one or more further parameters, or any combination thereof.

In addition to the individual acceleration sensor elements 28, the acceleration sensor units 26, 27 may also be configured as microsystem units. As a result, the acceleration sensor units 26, 27 available for the acquisition of movement data, acceleration data, or both movement and acceleration data of the patient 15 are compact. The acceleration sensor units 26, 27 may thus be disposed in a space-saving manner within local high-frequency antenna units 39. The antenna units 39 are configured to detect magnetic resonance signals and are positioned around a subregion of the patient 15 as, for example, a high-frequency head antenna unit or a high-frequency chest antenna unit on the patient 15 (see FIG. 2).

In one exemplary embodiment, the movement detection unit 25 (e.g., the individual acceleration sensor units 26, 27) may be configured as magnetic resonance-compatible for use together with the magnetic resonance apparatus. If the movement detection unit 25 is also used for further medical imaging apparatuses 10 (e.g., a PET apparatus, a computed tomography apparatus, or a combination thereof), the movement detection unit 25 may not be magnetic resonance-compatible.

Figure 4:
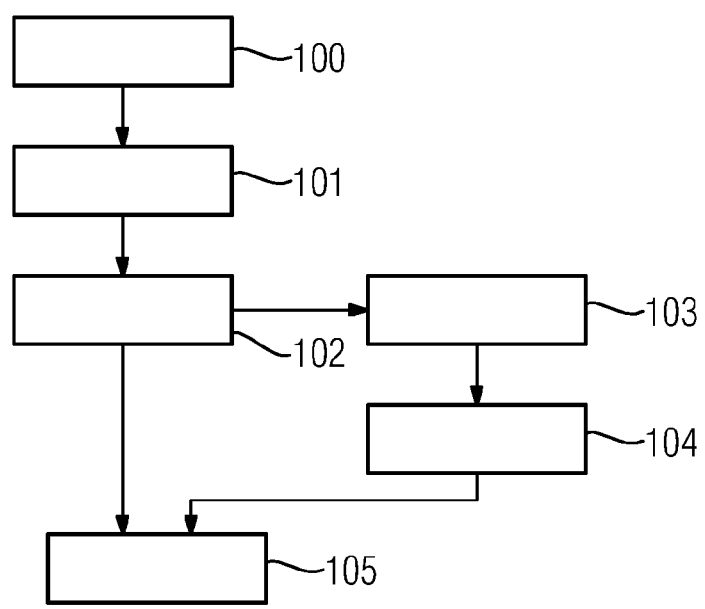
FIG. 4 shows a schematic flow diagram of a method for detecting patient movement during a medical imaging examination in accordance with one embodiment.

FIG. 4 shows a schematic sequence of one embodiment of a method for detecting patient movement during a medical imaging examination such as a magnetic resonance examination. In a positioning act 100, the patient 15 is first positioned on the patient support apparatus 16 and prepared for the magnetic resonance examination. Individual acceleration sensor units 26, 27 are disposed directly on the patient 15 (e.g., on the skin of the patient 15, on subregions of the patient 15 relevant to the magnetic resonance examination). In a further method act 101, the patient support apparatus 16 together with the patient 15 is then introduced into the patient-receiving region 14 of the magnetic resonance apparatus.

After introduction of the patient 15 into the patient-receiving region 14 of the magnetic resonance apparatus, the magnetic resonance examination is started, and medical image data is acquired in a further method act 102 by the magnet unit 11 together with local high-frequency antenna units 39. At the same time as the medical image data is being acquired, in a further method act 103, movement data, acceleration data, or both movement data and acceleration data is also acquired by the acceleration sensor units 26, 27. In a further method act 104, the movement data, acceleration data, or both movement and acceleration data from the acceleration sensor units 26, 27 is transmitted to the data evaluation unit 34 and evaluated at the data evaluation unit 34.

In a further method act 105, the movement data evaluated by the data evaluation unit 34 is transmitted to the system control unit 22, where the movement data is used for triggering, reconstructing, or both triggering and reconstructing the medical image data.

Although the invention has been illustrated and described in detail using the preferred exemplary embodiment, the invention is not restricted by the disclosed examples and other variations may be derived therefrom by the person skilled in the art, without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance imaging apparatus comprising:
   a detector unit;
   a patient-receiving region enclosed by the detector unit in a cylindrical manner; and
   a movement detection unit comprising at least one acceleration sensor unit operable to detect movement of a patient, the at least one acceleration sensor unit comprising a fastening element operable to fasten the at least one acceleration sensor unit to a subregion of the patient relevant to a medical imaging examination.

2. The magnetic resonance imaging apparatus of claim 1, wherein the at least one acceleration sensor unit comprises:
   an acceleration sensor element disposed on a microchip.

3. The magnetic resonance imaging apparatus of claim 1, wherein the at least one acceleration sensor unit comprises:
   at least one acceleration sensor element operable to detect movement of the patient along a single spatial direction.

4. The magnetic resonance imaging apparatus of claim 1, wherein the at least one acceleration sensor unit comprises:
   at least one acceleration sensor element operable to detect movement of the patient along at least two different spatial directions.

5. The magnetic resonance imaging apparatus of claim 1, wherein the at least one acceleration sensor unit comprises:
   at least one energy supply unit.

6. The magnetic resonance imaging apparatus of claim 1, wherein the fastening element comprises:
   an adhesion layer.

7. The magnetic resonance imaging apparatus of claim 1, wherein the movement detection unit comprises:

a data evaluation unit configured to evaluate movement data acquired via the at least one acceleration sensor unit.

8. The magnetic resonance imaging apparatus of claim 7, wherein the at least one acceleration sensor unit is wirelessly connected to the data evaluation unit.

9. The magnetic resonance imaging apparatus of claim 8, further comprising:
a system control unit configured to generate a trigger signal for medical image data acquisition as a function of the movement data evaluated by the data evaluation unit.

10. The magnetic resonance imaging apparatus of claim 8, further comprising:
a system control unit configured to generate a correction factor for an evaluation of medical image data as a function of the movement data evaluated by the data evaluation unit.

11. The magnetic resonance imaging apparatus of claim 3, wherein the at least one acceleration sensor unit comprises:
a further sensor element configured to detect a further patient parameter.

12. The magnetic resonance imaging apparatus of claim 4, wherein the acceleration sensor unit comprises:
a further sensor element configured to detect a further patient parameter.

13. A medical imaging apparatus comprising:
a patient-receiving region; and
a movement detection unit comprising at least one micro-electro-mechanical (MEMS) acceleration sensor comprising:
a fastening element operable to fasten the at least one MEMS acceleration sensor to a subregion of a patient relevant to a medical imaging examination, and
wherein the movement detection unit is configured to convert energy of the medical imaging apparatus within the patient-receiving region into electricity.

14. The medical imaging apparatus of claim 13, wherein the at least one MEMS acceleration sensor comprises:
at least one MEMS acceleration sensor element operable to detect movement of the patient along a single spatial direction.

15. The medical imaging apparatus of claim 13, wherein the at least one MEMS acceleration sensor comprises:
at least one MEMS acceleration sensor element operable to detect movement of the patient along at least two different spatial directions.

16. The medical imaging apparatus of claim 13, wherein the fastening element comprises:
an adhesion layer.

17. The medical imaging apparatus of claim 13, further comprising:
a system control unit configured to generate a trigger signal for medical image data acquisition as a function of movement data evaluated by a data evaluation unit.

18. The medical imaging apparatus of claim 13, further comprising:
a system control unit configured to generate a correction factor for an evaluation of medical image data as a function of movement data evaluated by a data evaluation unit.

19. The medical imaging apparatus of claim 13, wherein the medical imaging apparatus is a positron emission tomography apparatus.

20. The medical imaging apparatus of claim 13, wherein the medical imaging apparatus is a computed tomography apparatus.

* * * * *